(12) United States Patent
Sauer

(10) Patent No.: US 6,919,867 B2
(45) Date of Patent: Jul. 19, 2005

(54) METHOD AND APPARATUS FOR AUGMENTED REALITY VISUALIZATION

(75) Inventor: Frank Sauer, Princeton, NJ (US)

(73) Assignee: Siemens Corporate Research, Inc., Princeton, NJ (US)

( * ) Notice: Subject to any disclaimer, the term of this patent is extended or adjusted under 35 U.S.C. 154(b) by 245 days.

(21) Appl. No.: 10/109,129

(22) Filed: Mar. 28, 2002

(65) Prior Publication Data

US 2002/0163499 A1 Nov. 7, 2002

Related U.S. Application Data

(60) Provisional application No. 60/279,931, filed on Mar. 29, 2001.

(51) Int. Cl.$^7$ ................................................ G09G 5/00
(52) U.S. Cl. .................................. 345/8; 345/7; 345/9
(58) Field of Search ..................... 345/7, 8, 9; 359/630, 359/631, 633, 638; 382/128, 130, 131, 132, 133, 153, 154, 162, 171, 173, 278, 294

(56) References Cited

U.S. PATENT DOCUMENTS

| | | | | |
|---|---|---|---|---|
| 5,531,227 A | * | 7/1996 | Schneider | 600/425 |
| 5,740,802 A | * | 4/1998 | Nafis et al. | 600/407 |
| 6,204,974 B1 | * | 3/2001 | Spitzer | 359/630 |
| 6,351,573 B1 | * | 2/2002 | Schneider | 382/294 |

FOREIGN PATENT DOCUMENTS

WO    WO98/38908    * 9/1998

OTHER PUBLICATIONS

Takagi et al., "Development of a Stereo Video See–through HMD for AR Systems", IEEE & ACM Int. Symp. On Augmented Reality—ISAR 2000 (Munich, Germany, Oct. 5–6, 2000), pp. 68–77.

Sauer et al., "Augmented Workspace: designing an AR testbed", IEEE & ACM Int. Symp. On Augmented Reality—ISAR 2000 (Munich, Germany, Oct. 5–6, 2000) pp. 47–53.

"Video–see–through Head–mounted Displays for Augmented Reality at UNC", http://www.cs.unc.edu/~us/web/headmounts.htm.

State et al., "Superior Augmented Reality Registration by Integrating Landmark Tracking and Magnetic Tracking", http:/www.cs.unc.edu/~ us/hybrid.html.

Auer et al., "Building a Hybrid Tracking System: Integration of Optical and Magnetic Tracking" http://hci.rsc.rockwell.com/iwar/99/WebProceedings/Auer/.

U.S. Appl. No. 09/607,116 entitled "Method and Apparatus for Robust Optical Tracking with Beacon Markers".

* cited by examiner

*Primary Examiner*—Vijay Shankar

(57) ABSTRACT

A videoscope system comprises a pair of imaging cameras for capturing a stereoscopic view of a workspace, and a tracking camera for capturing a field of view including a marker structure, and a display for displaying the stereoscopic view of the workspace captured by the pair of imaging cameras and augmented with a computer graphic according to a position and orientation of the imaging cameras relative to the workspace. The videoscope system further comprises a processor for determining the position and orientation of the imaging cameras relative to the workspace based on the location of the marker structure in the field of view captured by the tracking camera, and an articulated support apparatus adapted to support a videoscope head comprising at least the imaging cameras.

37 Claims, 4 Drawing Sheets

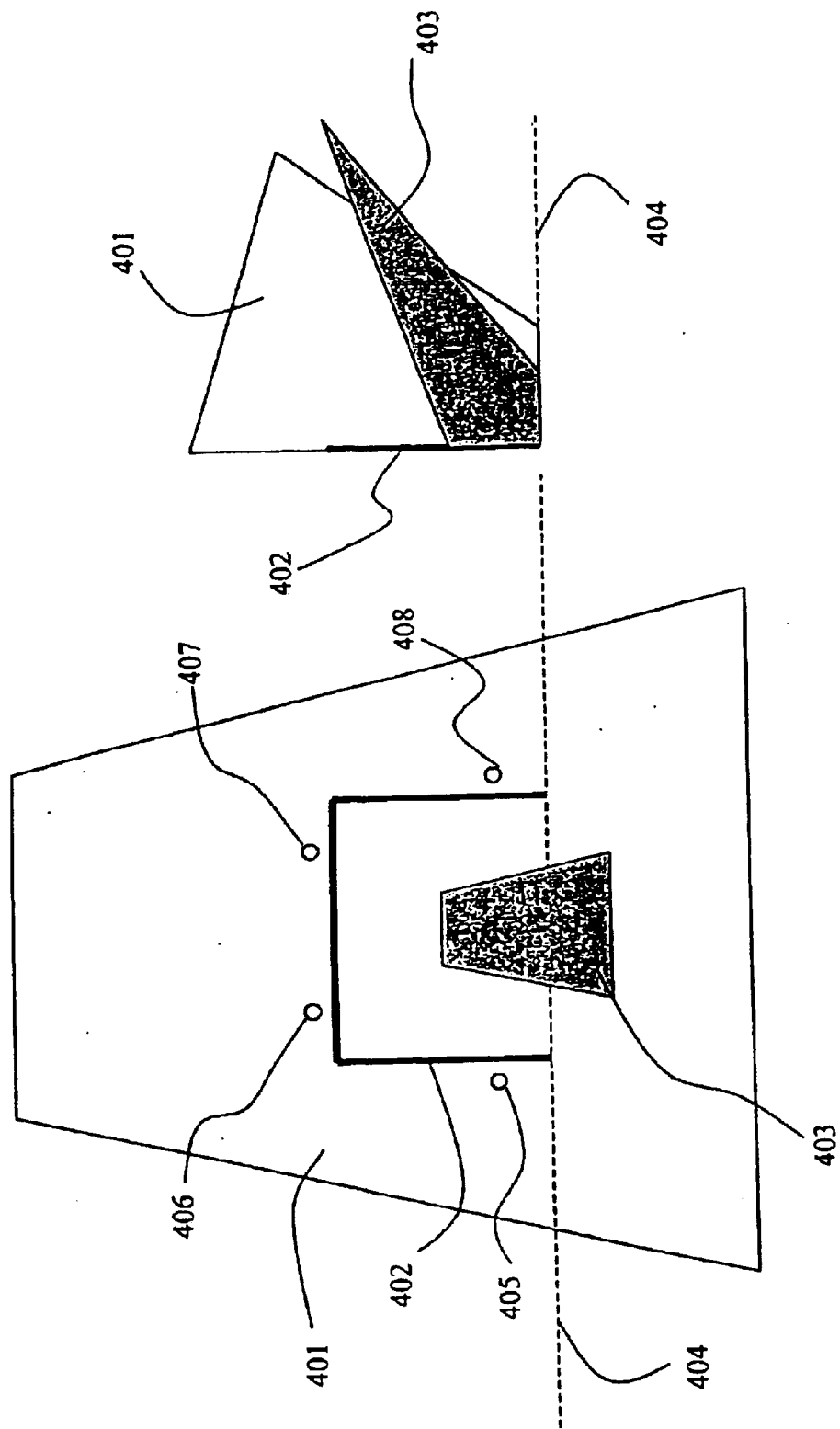

METHOD AND APPARATUS FOR AUGMENTED REALITY VISUALIZATION

Reference is hereby made to copending Provisional Patent Application No. 60/279,931, entitled Method and Apparatus For Augmented Reality Visualization, filed Mar. 29, 2001 in the name of Frank Sauer, of which priority is hereby claimed and whereof the disclosure is hereby incorporated by reference in the present application.

BACKGROUND OF THE INVENTION

1. Field of the Invention

The present invention relates to augmented reality, and more particularly to an externally supported videoscope for augmented reality implementations.

2. Discussion of Related Art

Virtual reality is used in many diverse fields, such as kitchen design and military training. Virtual reality immerses a user in a digital environment, where the user's perceptions of sight and sound are manipulated by a computer. While virtual reality provides inexpensive alternatives to building a mock-up of a kitchen or firing live ammunition during an exercise on a battlefield, virtual reality systems lack the sophistication of human perception.

Virtual reality systems have evolved into augmented reality based systems, where a user's perception of a real environment is augmented with information. FIG. 1 is a block diagram illustrating an augmented reality system wherein video images of the environment are combined with computer-generated graphics, according to the prior art. The system includes: a video camera 110; external trackers 112; two dimensional/three dimensional (2D/3D) graphics module 114; an image processing module 116; a pose calculation module 118; a graphics rendering module 120; a video and graphics overlay module 122; and a display 124. As is known, a 3D visual perception may be achieved through use of two cameras and a stereo display.

An augmented reality system can be used to provide guidance to a user, for example, providing information during a surgical procedure. A view of a patient's internal anatomical structures may be overlaid onto a real view of the patient. The internal structures are determined and shown in a graphical representation registered with the view of the real patient.

A head-mounted display (HMD) is a desirable means to display an augmented view to a user. Various HMDs are depicted at http://www.cs.unc.edu/~us/web/headmounts.htm. A HMD allows the user to vary the viewpoint by turning his or her head. However, HMDs are typically cumbersome, especially over longer periods. The weight of a HMD may put a significant strain on a user's neck and back, especially if the user assumes a pose with a tilted head.

The prior art proposes that the difference between the user's natural eye-point and the viewpoint of the video camera is a concern. The prior art proposes designs which attempt to align an imaging camera with the user's line of sight. Designs have been proposed to further include beam combiners to align the optical axis of a camera and a user, e.g., A. Takagai, S. Yamazaki, Y. Saito, and N. Taniguchi, "Development of a Stereo Video-See-Though HMD for AR Systems," IEEE and ACM Int. Symp. On Augmented Reality—ISAR 2000 (Munich, Germany, Oct. 5–6, 2000), pages 68–77. However, these systems do not address the comfort associated with wearing a HMD, particularly when the user assumes a pose with a tilted head.

For registration between the view of the real environment and the augmenting graphics, the user's viewpoint needs to be tracked. In prior art, head-mounted tracking cameras have been used for optical-see-through displays (where the user sees the real environment through a semitransparent display that shows additional graphics), but not for video-see-through displays. An example of an optical-see-through HMD with two head-mounted tracking cameras in conjunction with a magnetic tracker is described by Thomas Auer and Axel Pinz in "Building a Hybrid Tracking System: Integration of Optical and Magnetic Tracking", Proceedings of the 2nd IWAR'99, IEEE Computer Society, (IWAR'99, San Francisco, Oct. 20–21, 1999). In the case of video-see-through HMDs, a method has been proposed which uses the views captured by the imaging cameras for tracking, and a magnetic tracker. See State, Andrei, Gentaro Hirota, David T. Chen, William F. Garrett, and Mark A. Livingston. "Superior Augmented-Reality Registration by Integrating Landmark Tracking and Magnetic Tracking." Proceedings of SIGGRAPH 96 (New Orleans, La., Aug. 4–9, 1996); Computer Graphics Proceedings, Annual Conference Series 1996, ACM SIGGRAPH, pgs. 429–438. However, the tracking capabilities exhibited by the known prior art systems are not suitable in a practical setting for tasks needing precise graphical registration.

A video-see-through display can be head-mounted. Tracking, e.g., by optical means, can be added to enable augmented reality visualization. See: F. Sauer, F. Wenzel, S. Vogt, Y. Tao, Y. Gene, and A. Bani-Hashemi, "Augmented Workspace: Designing an AR Testbed," IEEE and ACM Int. Symp. On Augmented Reality—ISAR 2000 (Munich, Germany, Oct. 5–6, 2000), pages 47–53.

Within the field of virtual reality, Fakespace Labs Inc. offers the BOOM (Binocular Omni-Orientation Monitor) personal immersive display for stereoscopic visualization on a counterbalanced, motion-tracking support structure. The BOOM utilizes opto-mechanical shaft encoders for tracking. Mechanical tracking requires the boom to be stiff to achieve precise measurements, this can increase the costs associated with a boom mechanism. A boom can be directed by a user's hand or connected to the user's head to free the hands. However, for applications, which need extended use, a head-mounted device can tire the user. In addition, a head-mounted solution is also not very practical if the display needs to be put on and taken off frequently.

For augmented reality applications needing both precise measurements and comfortable use, such as in an operating room, no known system currently exists. Therefore, a need exists for an externally supported video-see-through display having precise tracking.

SUMMARY OF THE INVENTION

A videoscope system comprises a pair of imaging cameras for capturing a stereoscopic view of a workspace, and a tracking camera for capturing a field of view including a marker structure, the tracking camera having a fixed position and orientation relative to the pair of imaging cameras. The videoscope system comprises a display for displaying the stereoscopic view of the workspace captured by the pair of imaging cameras and augmented with a computer graphic according to a position and orientation of the imaging cameras relative to the workspace. The videoscope system further comprises a processor for determining the position and orientation of the imaging cameras relative to the workspace based on the location of the marker structure in the field of view captured by the tracking camera, and an articulated support apparatus adapted to support a videoscope head comprising at least the imaging cameras.

BRIEF DESCRIPTION OF THE DRAWINGS

Preferred embodiments of the present invention will be described below in more detail, with reference to the accompanying drawings:

FIG. 4a is an illustration of the fields of view as captured by an imaging camera and a tracking camera according to an embodiment of the present invention;

FIG. 4b is an illustration of the fields of view of an imaging camera and a tracking camera as seen from the side, according to an embodiment of the present invention.

DETAILED DESCRIPTION OF PREFERRED EMBODIMENTS

According to an embodiment of the present invention, a videoscope system comprises a video means, e.g., stereo pair of imaging cameras, a display means, preferably a stereo display, a mechanical support means, and tracking means. The display can be a video-see-through display with an external mechanical support. For a head-mounted implementation, the external mechanical support can partially support the weight of a head-mounted display when it is worn. The external mechanical support can completely carry the display-camera-assembly during use. In both cases, the user can easily step back from the videoscope or swing it out of position. In this "non-use" state the videoscope is completely self-supporting.

According to an embodiment of the present invention, a videoscope can provide augmented reality image guidance for surgical procedures, for example, as described in U.S. patent application Ser. No. 09/971,554, entitled AUGMENTED REALITY VISUALIZATION DEVICE, incorporated herein by reference. Thus, data, such as a Magnetic Resonance Imaging (MRI) scan, can be shown in-situ, overlaid on a surgeon's view of a patient. The internal structures can be directly presented in the surgeon's workspace in a registered fashion. The surgeon can wear a head-mounted display and can examine the spatial relationship between the anatomical structures from varying positions in a natural way. Thus, a surgeon can better focus on a task and perform an operation more precisely and confidently without the need for referring to a remote display.

Figure 1:
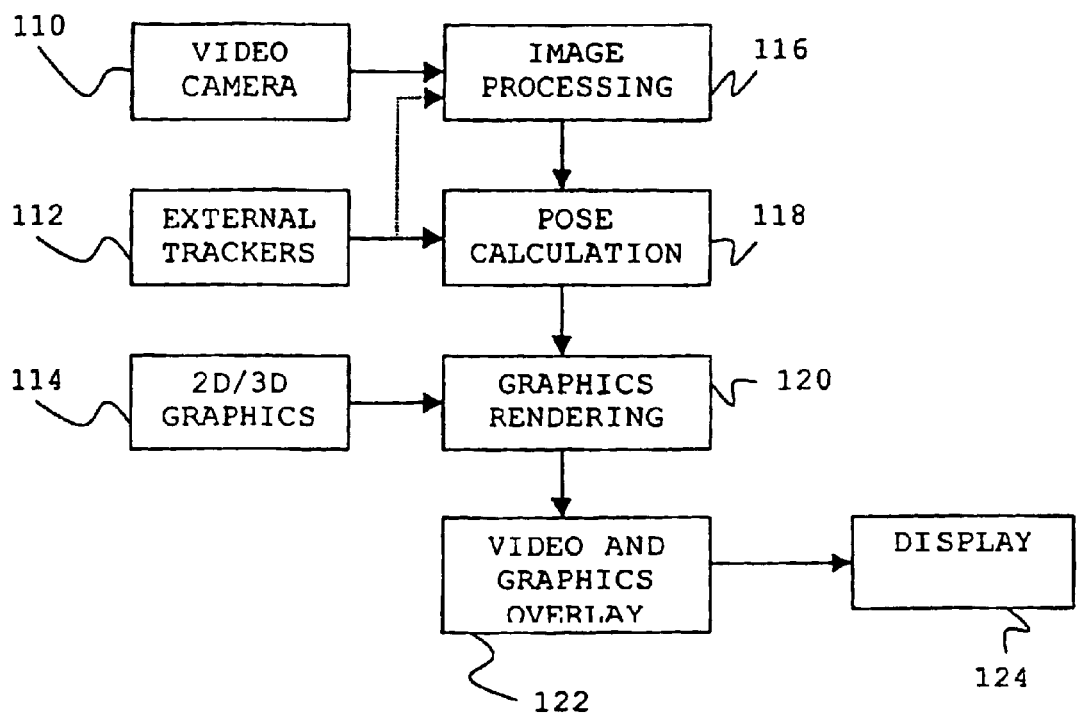
FIG. 1 is a block diagram illustrating an augmented reality system according to an embodiment of the present invention.
Figure 2B:
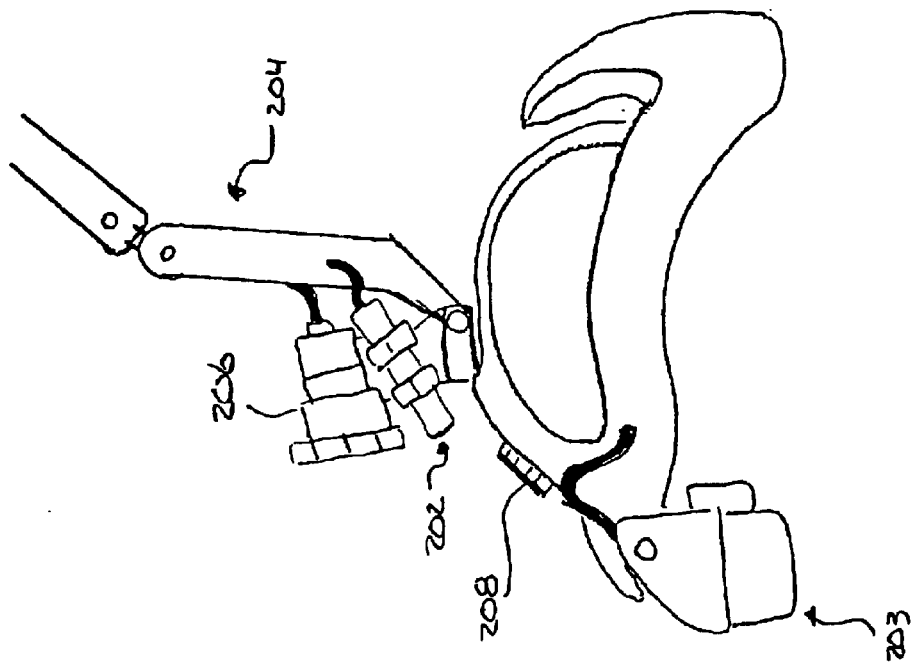
FIG. 2b is a diagram of a video-see-through display according to an embodiment of the present invention.
Figure 2A:
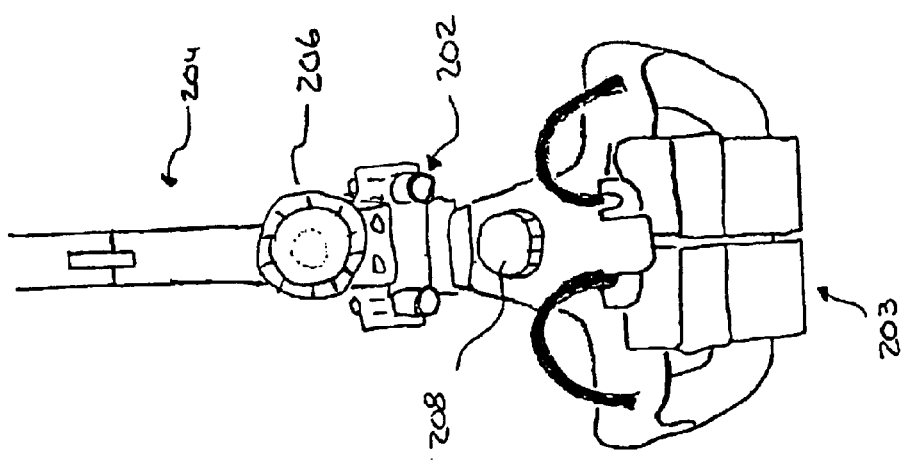
FIG. 2a is a diagram of a video-see-through display according to an embodiment of the present invention.

Referring to FIGS. 2a and 2b, a videoscope comprises a pair of stereo video cameras 202 and stereo display 203 and mechanical 204 support such as an articulated arm. Any number of video cameras can be provided depending on the viewing needs. For augmented reality applications the videoscope system comprises a tracking means 206 and computer processor for tracking and visualization. The tracking means 206 can have a fixed position with respect to the imaging cameras 202.

Figure 3:
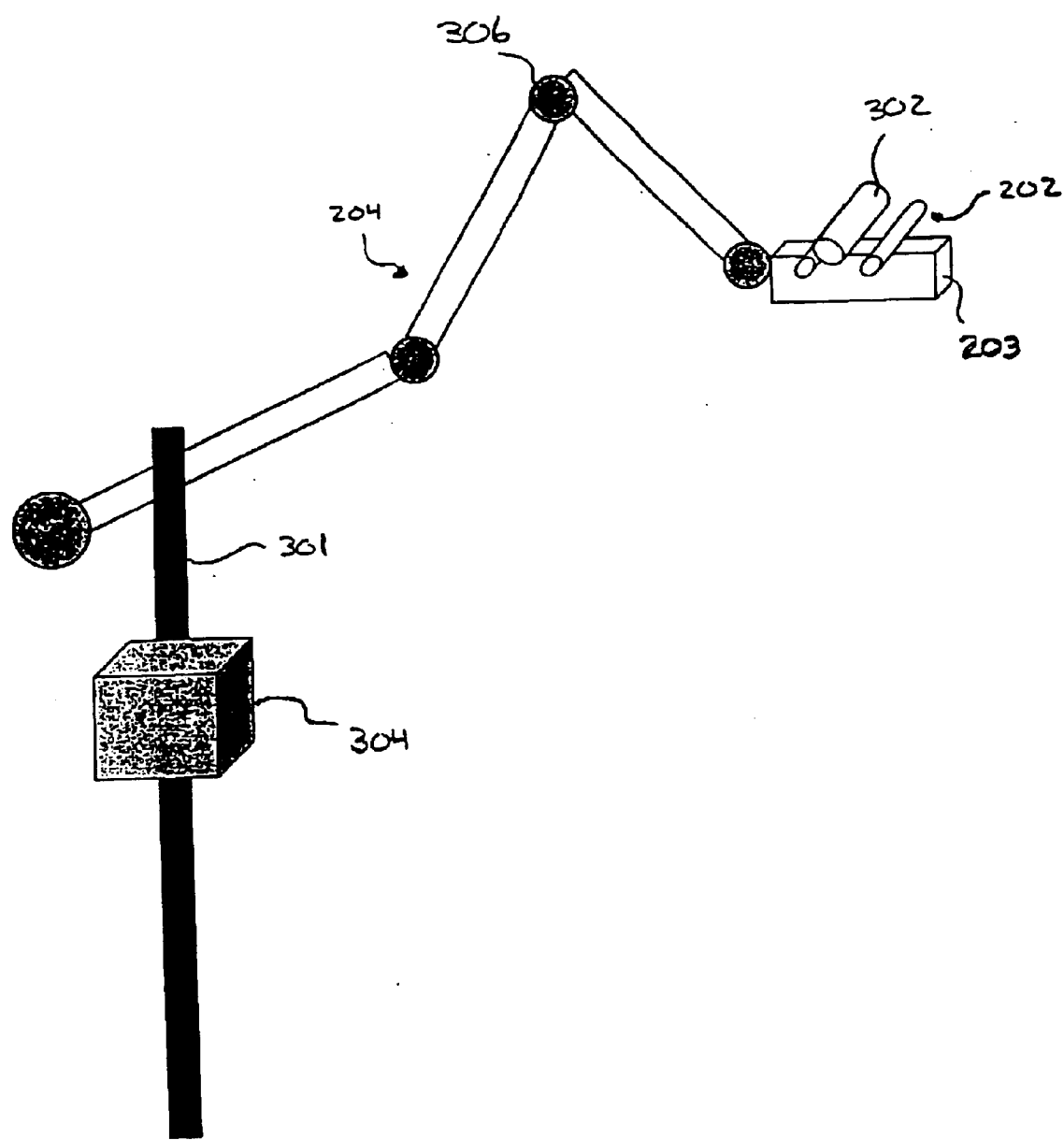
FIG. 3 is a diagram of a video-see-through display according to another embodiment of the present invention.

FIG. 3 illustrates a videoscope system comprising a support 301, for example, a wall, a ceiling or portable cart. A videoscope head comprises a stereo pair of video cameras 202 and stereo display 203. The videoscope head is connected to a mechanical support 204 such as an articulated arm. An optical tracking system implementing remote tracking cameras, for example, mounted around a workspace can track the videoscope head. The videoscope head can be adapted to comprise one or more elements, including, for example, the imaging cameras, the display, and a tool.

The imaging cameras may be pitched at an angle. The angle of the imaging cameras preferably enables a user to maintain a comfortable and relaxed posture. For example, a surgeon may prefer to pitch the imaging cameras downward at a particular angle, with a view of a patient. Thus, the surgeons head and neck posture can remain substantially upright throughout the procedure. The angle between the optical axes of the imaging camera 202 and the viewing direction of the user can be between about 0 degrees and about 60 degrees. The pitch angle of the imaging cameras 202 can be between about 0 degrees and greater than about 60 degrees down angle.

The videoscope system can comprise an imaging tool, for example, a graphics application for allowing the user to enhance or adjust the views with color, or text. In addition, the user may select objects in the workspace, or include graphical objects as guides. Referring to FIG. 3, a surgical light is another example of a tool 302. The light can illuminate the field of view of the imaging cameras. The light source can be mounted close to the imaging cameras. Thus, the light can reach into narrow openings into which the cameras are directed.

According to an embodiment of the present invention a videoscope system can comprise a remote display 304. A remote display can be used where, for example, the imaging cameras are connected to a remotely controlled arm. Thus, a user can view an area of interest from the viewpoint of an instrument connected to the arm, wherein the instrument is in the proximity of the imaging cameras, for example, a few centimeters apart. The videoscope system can comprise a control means, wherein the control means can be analog and/or digital, e.g., a pair of joysticks for controlling the pose of an articulated arm. The control means, such as a handle connected to the arm, can provide the user control over the movement of the arm. The control means can be configured to remotely control the mechanical support and/or tools, for example, through the use of electromagnetic motors at the joints of the mechanical support. In addition, the control means can be used to adjust the attributes of the imaging cameras and other tools, such as a light source.

The mechanical support 204 allows easy movement of videoscope head in a range of poses, and locking of these poses. The videoscope system can comprise a means for locking the videoscope head in place. For example, a mechanical means such as a clamp or ratchet mechanism or an electromagnetic lock at each joint, e.g., 306, of the support mechanism. Movement can be guided by hand or head movements. The support can be connected to any suitable surface or carriage, for example, a wall, a ceiling, or a moveable cart.

According to an embodiment of the present invention, a videoscope can be understood as an operating microscope, where the direct optical observation has been replaced by an indirect observation via the electronic camera-display combination. The concept of the videoscope is not limited to high magnification applications and can be implemented in scenarios needing various levels of magnification including no magnification. Different videoscopes can be made for different magnifications and field-of-views. The level of magnification can be controlled via an optical/digital zoom function or via switching of camera-lens combination. For correctly registering the graphics overlay onto the video images, the optomechanical system comprises sensors that report the state of all the relevant parameters like zoom factor, etc.

In the case of head guidance, the videoscope head can be designed similarly to a head-mounted display. The user puts it on his head and tightens it with a mechanism like an adjustable headband or chin strap, for example, 208 in FIGS. 2a and 2b. The user can wear a headband to which the videoscope can be docked at a predetermined pose. A mechanical guide, e.g., with a female part attached to the head band and a male part attached to the videoscope head (or vice versa), can bring the videoscope into the predetermined pose. A mechanical latch or a magnetic/electromagnetic coupling can be used to attach the headband and videoscope. The videoscope can be implemented in conjunction with other systems, such as ultrasound imaging devices, Computerized Axial Tomography (CAT) scanners and MRI scanners. Thus, the videoscope can provide in-situ visualization of a patient using the images captured by these and other systems. The videoscope can be implemented as a guidance system for directing the use of instruments associated in these devices. For example, using an augmented view with in-situ visualization of an ultrasound image, a user can guide a needle towards a target.

Tracking is needed for in-situ visualization. The viewpoint of the imaging cameras is needed to precisely overlay graphics as seen from the viewpoint of a user. Tracking can be by, for example, mechanical, magnetic, inertial, or optical means. Optical tracking systems based on stereo-camera system are commercially available. A multicamera system, wherein each camera has a view of the videoscope and workspace can be used for tracking the videoscope. Markers can be attached to the videoscope for tracking by these remotely mounted cameras. Alternatively, a tracking camera can be mounted to the videoscope, for example, 206 in FIGS. 2a and 2b, for tracking markers in or around the workspace, for example, as shown in FIG. 4.

A videoscope according to the present invention should allow relaxed work posture. In a surgical scenario, e.g., the displays can be straight so that the surgeon does not have to tilt down his head, while the video cameras are tilted downward.

A computer processor connected to the videoscope can render, in real time, an augmented stereo view. The processor can receive video images from the imaging cameras, video images for determining pose information from the tracking camera, and stored volume and/or 3D surface data relating to the virtual view. The virtual view can be rendered according to the camera pose information, determined by the processor, and blended with the corresponding video images. The augmented images can be displayed stereoscopically.

Referring to FIGS. 4a and 4b, the field of view of the tracking camera 401 includes four non-collinear marker points 405–408 on the workspace frame 402. Any number of markers can be used, preferably a number is used to enable tracking in six degrees of freedom. The markers define a common coordinate system for the workspace. The markers are used to determine the pose of the tracking camera in the common coordinate system. Knowing the relationship between the tracking and imaging cameras, the pose of imaging cameras can be determined. Therefore, augmenting graphics objects may be rendered or registered into stereo video images from the video viewpoints of the imaging cameras. The graphics can appear anchored in the augmented scene.

Having described embodiments for an augmented reality system, it is noted that modifications and variations can be made by persons skilled in the art in light of the above teachings. It is therefore to be understood that changes may be made in the particular embodiments of the invention disclosed which are within the scope and spirit of the invention as defined by the appended claims. Having thus described the invention with the details and particularity required by the patent laws, what is claimed and desired protected by Letters Patent is set forth in the appended claims.

What is claimed is:

1. A videoscope system for generating and displaying an augmented reality view to a user comprising:

a pair of imaging cameras for capturing a stereoscopic video view of a workspace;

at least one tracking apparatus for determining a pose of the imaging camera with respect to the workspace;

a processor for compositing the stereoscopic view by overlaying computer graphics onto said stereoscopic video view in correspondence to the pose of the imaging cameras;

a display for displaying the stereoscopic view of the workspace captured by the pair of imaging cameras and augmented with said computer graphic according to a position and orientation of the imaging cameras relative to the workspace; and a support apparatus adapted to support the weight of a videoscope head comprising at least the imaging camera and the display, wherein the support apparatus can be positioned into a plurality of positions by a user so that the user can look through the videoscope head to see a plurality of augmented reality views of the workspace.

2. The system of claim 1, wherein the pair of imaging cameras is oriented at a downward pitch angle greater than about 25 degrees from horizontal.

3. The system of claim 1, wherein the display can be selectively positioned at a pitch, relative to the videoscope head and the pair of imaging cameras.

4. The system of claim 1, wherein the at least one tracking apparatus is fixed to the videoscope head.

5. The system of claim 1, wherein the support apparatus comprises a plurality of joints.

6. A supported videoscope display system for generating and displaying an augmented reality view to a user comprising:

an imaging camera for capturing a view of a workspace;

a tracking means for determining a pose of the imaging camera with respect to the workspace;

a display for displaying the view of the workspace captured by the imaging camera and augmented with computer graphics according to the pose of the imaging cameras;

a support apparatus adapted to support the weight of a videoscope head comprising the imaging camera, the support apparatus being manually positioned by a user so that the user can look through the videoscope head to see a plurality of augmented reality views of the workspace; and a processor coupled to the imaging camera, the tracking means and the display for creating the augmented view as a combination of video images and graphics.

7. The system of claim 6, further comprising a second imaging camera thereby providing a pair of imaging cameras adapted to provide a stereo view of the workspace.

8. The system of claim 6, wherein the tracking means comprises a tracking camera for capturing a field of view including a marker structure.

9. The system of claim 8, wherein the tracking camera is positioned at a fixed orientation relative to the imaging camera.

10. The system of claim 8, wherein the tracking means further comprises a processor for determining the pose of the imaging camera relative to the workspace according to a view captured by the tracking camera.

11. The system of claim 6, wherein the videoscope head further comprises the display.

12. The system of claim 11, wherein a pitch angle of the display facilitates a substantially erect head posture, wherein the pitch angle of the display can be one of fixed and adjustable.

13. The system of claim 6, wherein the display is remote to the imaging camera.

14. The system of claim 6, further comprising a tool connected to the videoscope head.

15. The system of claim 14, wherein the tool is a light.

16. The system of claim 6, further comprising a medical device, wherein the videoscope is a guidance system for directing the positioning of the medical device.

17. The system of claim 6, wherein the support apparatus further comprises a mechanical guide for positioning and fixing a use's head in a substantially predetermined pose relative to the display, wherein the support apparatus can be positioned by head movements.

18. The system of claim 16, wherein the mechanical guide comprises one of a headband and a chin strap to be worn by a user.

19. The system of claim 6, wherein the imaging camera further comprises at least one of, a zoom means, an auto-focus means, and a magnification means.

20. The system of claim 6 further comprising a controller for controlling movement of the support apparatus.

21. The system of claim 20 wherein the controller is one or more handles that are connected to the support apparatus, the handles allowing a user to manually move the support apparatus and position the videoscope.

22. The system of claim 20 wherein the controller is a pair of joysticks for controlling a pose of the support apparatus.

23. The system of claim 20 wherein the controller is configured to remotely control the movement of the support apparatus.

24. The system of claim 23 wherein the controller includes an electromagnetic motor that is located at one or more of the joints of the support apparatus.

25. The system of claim 6 wherein the support apparatus is connected to a ceiling of a room in which the videoscope system is used.

26. The system of claim 6 wherein the support apparatus is connected to a wall of a room in which the videoscope system is used.

27. The system of claim 6 wherein the support apparatus is connected to a portable cart.

28. The system of claim 1 wherein the support apparatus is articulated.

29. The system of claim 5 wherein at least one joint of the support apparatus comprises a lock to fix a position of the videoscope head supported by the support apparatus.

30. The system of claim 1 wherein the at least one tracking apparatus is a camera for capturing a field of view including a marker structure.

31. The system of claim 30, wherein the tracking means further comprises a processor for determining the pose of the imaging camera relative to the workspace according to a view captured by the tracking camera.

32. The system of claim 1 wherein the marker structure is fixed to the videoscope head.

33. The system of claim 6 wherein the support apparatus is articulated.

34. The system of claim 6 wherein the support apparatus comprises a plurality of joints.

35. The system of claim 33 wherein at least one joint comprises a lock to fix a position of the videoscope head supported by the support apparatus.

36. The system of claim 1 wherein the support apparatus can be manually moved into a plurality of positions by the user.

37. The system of claim 1 wherein the support apparatus is automatically moved into a plurality of positions.

* * * * *